United States Patent [19]

Heki

[11] 4,435,644

[45] Mar. 6, 1984

[54] RADIOACTIVE EFFLUENT GAS MONITORING APPARATUS

[75] Inventor: Hideaki Heki, Yokohama, Japan

[73] Assignee: Tokyo Shibaura Denki Kabushiki Kaisha, Kawasaki, Japan

[21] Appl. No.: 283,105

[22] Filed: Jul. 13, 1981

[51] Int. Cl.³ ............................................. G01N 21/01
[52] U.S. Cl. .................................. 250/435; 250/432 R
[58] Field of Search ............... 250/430, 432, 435, 438; 376/250, 253

[56] References Cited

U.S. PATENT DOCUMENTS 3,341,421 9/1967 Kägi ................................... 376/250
3,769,505 10/1973 Lee et al. ............................ 250/430
4,147,587 4/1979 Utamura et al. .................... 376/253

OTHER PUBLICATIONS

IAEA-SM-217/7 P367, A Krypton-85 Monitoring System with Permselective Membranes: S. Takamatsu; 1978.

Primary Examiner—Bruce C. Anderson
Attorney, Agent, or Firm—Oblon, Fisher, Spivak, McClelland & Maier

[57] ABSTRACT

An effluent gas monitoring apparatus for detecting radioactivities in water, carbon dioxide, and rare gases recovered by introducing the radioactive effluent gas to a water recovery section, a carbon dioxide recovery section and, if necessary, a rare gas concentration section which are arranged parallel to each other. The capacities, scales and gas flow rates of the respective sections which are arranged parallel to each other may be freely selected.

11 Claims, 11 Drawing Figures

RADIOACTIVE EFFLUENT GAS MONITORING APPARATUS

BACKGROUND OF THE INVENTION

The present invention relates to an apparatus for monitoring the amount of radioactive rare gases such as $^3H$, $^{14}C$, and $^{85}Kr$ in effluent gas discharged from nuclear facilitates.

Effluent of radioactive waste material from a nuclear power plant or other facilities which handle radioactive substances must be strictly monitored to protect our environment from radioactive pollution. Accordingly, techniques are demanded for measuring at very low levels the concentration of the radioactive substance contained in the material released from these facilities or in the surrounding environment. In particular, $^3H$, $^{14}C$, and $^{85}Kr$ are nuclides which have long half-lives even at low concentration. Therefore, their concentration must be measured and monitored even at very low concentrations.

A conventional effluent gas monitoring apparatus has been proposed in which are serially arranged an oxidizing section, a water separating section, a carbon dioxide separating section, and, if necessary, a rare gas concentrating section. Part of the effluent gas from the nuclear facility is introduced to the oxidizing section where carbon monoxide, hydrogen, hydrogen carbide and so on contained in the gas are converted to water and carbon dioxide. The oxidized gas is introduced to the water separating section where the water in the gas is solidified or condensed by cooling for separation. The gas from which water has been removed is introduced to the carbon dioxide separating section and is passed through a carbon dioxide absorbing solution such as monoethanolamine or the like to separate the carbon dioxide in the gas by absorption. The separated water and carbon dioxide are recovered and are measured for their respective $^3H$ and $^{14}C$ contents by liquid scintillation counters. If necessary, the gas from which the water and carbon dioxide has been separated is introduced to the radioactive rare gas concentrating section to concentrate $^{85}Kr$ or the like for measuring the concentration thereof.

However, since the water separating section, the carbon dioxide separating section, and the rare gas concentrating section are serially arranged with such a conventional apparatus, the flow rates and capacities of each section may not be determined independently of each other. For example, when the effluent gas is passed through the rare gas concentration section at a flow rate necessary for measuring $^{85}Kr$, this flow rate becomes higher than the optimum flow rate for the water separating section and for the carbon separating section. Thus, for obtaining better efficiency, the capacity or scale of the apparatus must be increased. Although the optimum flow rate at the water separating section changes according to the time of year and weather conditions, the flow rate at this section cannot be changed independently of the other sections with the serial arrangement. Furthermore, the amine-type absorbing solution such as monoethanolamine or phenylethylamine used for absorption of carbon dioxide becomes mixed with the exhaust gas from the carbon dioxide separating section and is then adsorbed or condensed within the next rare gas condensing section and might cause corrosion, particularly of rubber parts. Since these amine-type absorbing solutions are toxic, direct release into the air of the exhaust gas containing them poses an environmental pollution problem. As for the monoethanolamine, it is known to cause disorders in skin, mucous membranes and respiratory organs. $LD_{50}$ for rats is reported to be 2,140 mg/kg in the case of oral administration and 981 mg/kg in interperitoneal administration.

SUMMARY OF THE INVENTION

It is an object of the present invention to provide a radioactive effluent gas monitoring apparatus which is capable of efficiently recovering the water and carbon dioxide in the effluent gas and efficiently concentrating rare gases to measure radioactivity, by allowing optimum flow rates and capacities for the water separating section, the carbon dioxide separating section, and the rare gas concentrating section.

It is another object of the present invention to provide a radioactive effluent gas monitoring apparatus which eliminates adverse effects due to the amine-type carbon dioxide absorbing solutions such as monoethanolamine.

In order to achieve the above and other objects, there is provided according to the present invention a guide line for guiding radioactive effluent gas from a nuclear facility, an $H_2O$ recovery section which separates $^3H$ from the effluent gas in the form of water, a $CO_2$ recovery section which is arranged parallel to the $H_2O$ recovery section and which separates $^{14}C$ in the form of carbon dioxide, branch lines which separately feed the effluent gas from the guide line to the $H_2O$ recovery section and to the $CO_2$ recovery section, a line for joining discharged gases from the $H_2O$ recovery section and the $CO_2$ recovery section for refluxing to the nuclear facility, and means for detecting radioactivity in the recovered $H_2O$ and $CO_2$.

Preferably, the monitoring apparatus of the present invention further includes a rare gas concentrating section which is arranged parallel to the $H_2O$ recovery section and the $CO_2$ recovery section and which concentrates the radioactive rare gases contained in the effluent gas, and another detecting means for detecting the radioactivity in the concentrated rare gases.

In accordance with the present invention, since the $H_2O$ recovery section, the $CO_2$ recovery section, and the rare gas concentrating section are arranged parallel to each other, the flow rates of the gas, capacities and so on of the respective sections may be determined independently of each other, and the respective sections may thus be operated independently of each other. Accordingly, the overall apparatus may be made compact in size, and maintenance and inspection become easy.

DETAILED DESCRIPTION OF THE PREFERRED EMBODIMENTS

Figure 1:
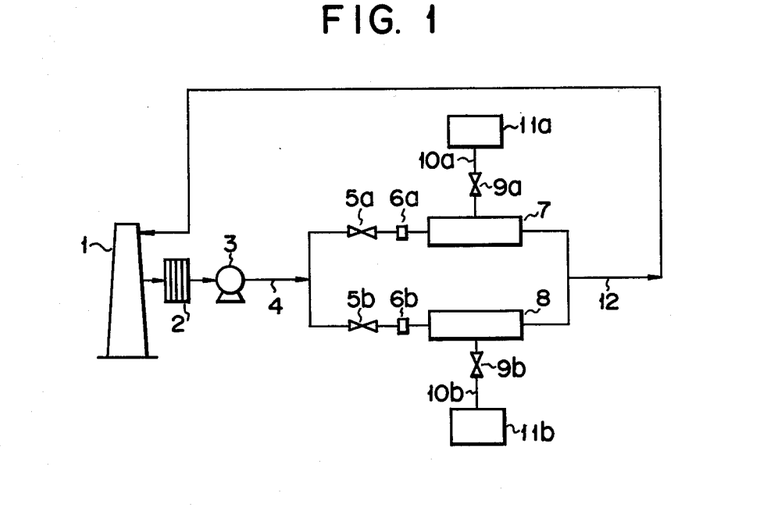
FIG. 1 is a system diagram showing an embodiment of a monitoring apparatus of the present invention wherein an $H_2O$ recovery section and a $CO_2$ recovery section are arranged parallel to each other.

The first embodiment will be described with reference to FIG. 1. The radioactive effluent gas sampled from a nuclear reactor stack 1 passes through a filter 2 and is guided to a guide line 4 by a pump 3. The guide line 4 branches to two lines; one communicates with an $H_2O$ recovery section 7 through a valve 5a and a flowmeter 6a where the water in the guided effluent gas is separated and recovered by cooling or adsorption. The water collected for a predetermined time is recovered through a valve 9a and a line 10a, and a concentration of radioactive $^3H$ is detected by a detecting means such as a liquid scintillation counter. The other line communicates with a $CO_2$ recovery section 8 through a valve 5b and a flowmeter 6b where carbon dioxide in the gas is separated and recovered by absorption or adsorption. The collected carbon dioxide is recovered through a valve 9b and a line 10b and its concentration of radioactive $^{14}C$ is detected by a detecting means 11b such as a liquid scintillation counter. The exhaust gas from the $H_2O$ recovery section 7 and the $CO_2$ recovery section 8 is released into the air or returned to the effluent system of the nuclear reactor through a line 12. Although an oxidizing section is not shown in this embodiment, such an oxidizing section is preferably inserted in the guide line 4 for converting carbon monoxide, hydrogen and hydrogen carbide in the effluent gas to water and carbon dioxide.

As the $H_2O$ recovery section, an apparatus may be adopted which cools the recovery chamber with a cooler to condense and solidify the water, and which elevates the temperature for melting the ice after a predetermined period of time; or an apparatus which adsorbs the water to separate and recover it utilizing an adsorbent such as a synthetic zeolite (e.g., trade name "Molecular Sieve", manufactured by Linde Co.) or a silica gel and which desorbs the water by elevating the temperature after a predetermined period of time and then recovers it with a separate recovery tank. As the $CO_2$ recovery section, an apparatus may be adopted which brings the effluent gas in contact with a $CO_2$ absorbing solution such as monoethanolamine and phenylethylamine by a method such as gas bubbling or the like to absorb the $CO_2$ in the gas; or an apparatus which adsorbs and recovers $CO_2$ with an adsorbent such as a synthetic zeolite, active carbon or the like, and which desorbs it by elevating the temperature after a predetermined period of time and recovers it with a separate recovery tank.

With the adoption of these apparatuses, the $H_2O$ recovery section and the $CO_2$ recovery section may be operated independently of each other. Consequently, even when the effluent gas is passed at a flow rate of 3 l/min through the $H_2O$ recovery section, it need not be passed at that flow rate through the $CO_2$ recovery section as in the case of the conventional apparatus of the serial arrangement. For example, since the carbon dioxide content of the gas is large and the carbon dioxide is easy to recover, the flow rate at the $CO_2$ recovery section may be reduced to 1 l/min. Therefore, the capacity of the $CO_2$ recovery section may be ⅓ that of the conventional apparatus of the serial arrangement, and the operation and control of the respective sections are easy.

Figure 2:
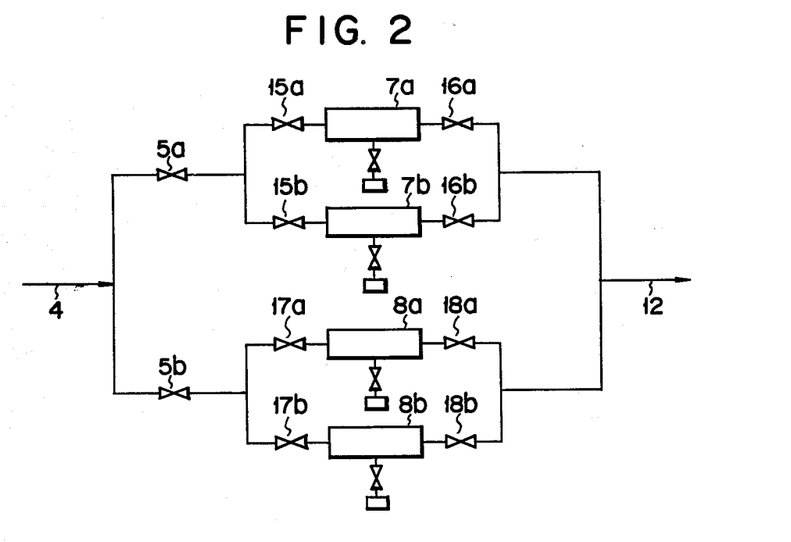
FIG. 2 is a system diagram showing another embodiment of the apparatus of the present invention having the $H_2O$ recovery section and the $CO_2$ recovery section.

The second embodiment is shown in FIG. 2. This apparatus is characterized in that two each of the $H_2O$ recovery sections and the $CO_2$ recovery sections as shown in FIG. 1 are arranged parallel to each other. In this apparatus, water and carbon dioxide may be continuously recovered by alternate switching of valves 15a and 15b, and valves 16a and 16b, and valves 17a and 17b, and valves 18a and 18b. Next, the mode of operation with this apparatus will be described. One $H_2O$ recovery section 7a is cooled to $-50°$ C. by a cooler, and one $CO_2$ recovery section 8a is filled with 105 cc of monoethanolamine. The effluent gas containing water and $CO_2$ is supplied to the apparatus to trap the water and $CO_2$. After a predetermined period of time, the valves 15a, 16a, 17a and 18a are closed, the temperature of the $H_2O$ recovery section 7a is elevated to drain-recover the trapped water, and at the $CO_2$ recovery section 8a, the monoethanolamine solution is drain-recovered. Simultaneously, the other $H_2O$ recovery section 7b is cooled to $-50°$ C. to trap the water, and the other $CO_2$ recovery section 8a is filled with 105 cc of the monoethanolamine to recover the $CO_2$. In this manner, two pairs of $H_2O$ recovery sections and $CO_2$ recovery sections are alternately switched to continuously recover $H_2O$ and $CO_2$. An example is shown in Table 1 below.

TABLE 1

| | $H_2O$ recovery section | $CO_2$ recovery section |
|---|---|---|
| Flow rate of feed gas [Nl/min] | 4.0 | |
| Flow rate at each section [Nl/min] | 3.0 | 1.0 |
| Composition $H_2O$ of feed gas $CO_2$ Air | 10,720 ppm 300 ppm Balance | |
| Recovery time [days] | 28 | |
| Switching frequency | Once/day | Once/week |
| Temperature for melting $H_2O$ [°C.] | 40 | — |
| Recovered amount [cc] | 1,030 (Water) | 406 (Monoethanolamine solution) |

It is seen from this table that the capacity of the $CO_2$ recovery section may be reduced to ⅓ the capacity when it is serially arranged with the $H_2O$ recovery section. Due to the reduction in the capacity of the $CO_2$ recovery section, consumption of the $CO_2$ recovery solution such as monoethanolamine may be vastly reduced.

Figure 3:
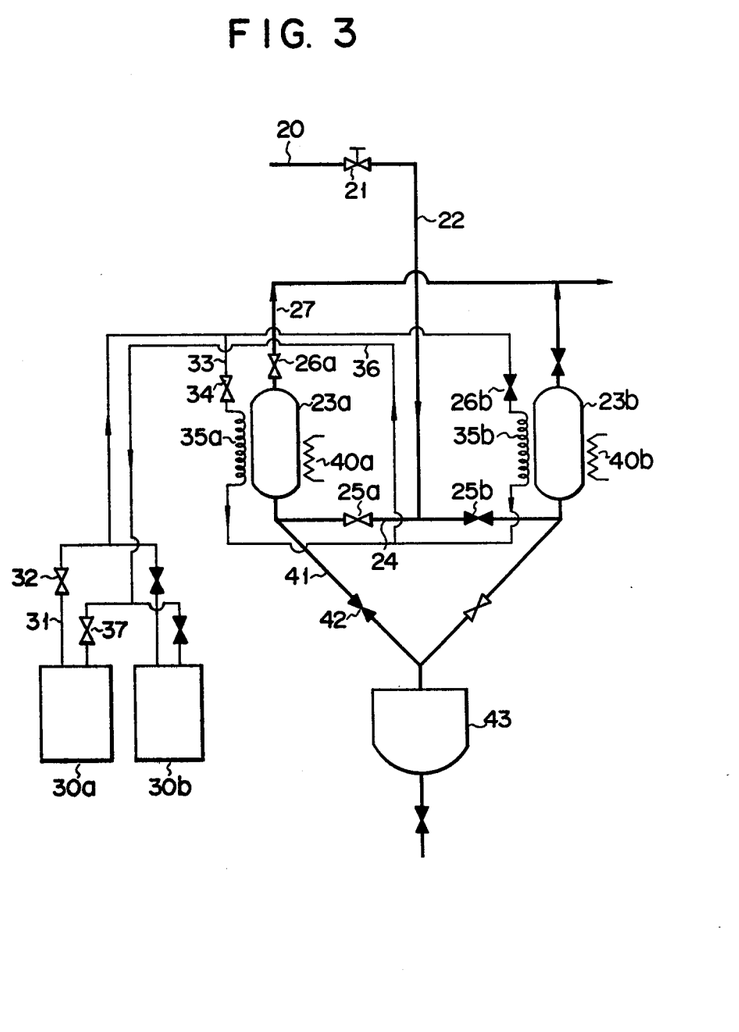
FIG. 3 is a system diagram showing an embodiment of the $H_2O$ recovery section.

An embodiment of the parallel-arranged $H_2O$ recovery sections in FIG. 2 will be shown in FIG. 3. The gas introduced through a gas guide line 20, a flow control valve 21, and a pipe 22 is fed to one $H_2O$ recovery trap 23a of a pair of $H_2O$ recovery traps through a pipe 24 and a valve 25a. The water contained in this gas is cooled to be solidified and is trapped by the $H_2O$ recovery trap 23a in the form of frost or ice. The gas eliminated of the water is guided to an outlet port or a stack through a valve 26a and a pipe 27. Meanwhile, a coolant from one cooler 30a of a pair of coolers 30a and 30b is supplied through a pipe 31, a valve 32, a pipe 33 and an expansion valve 34 to a cooling coil 35a of the $H_2O$ recovery trap 23a to cool it. The coolant is thereafter refluxed to the cooler 30a through a pipe 36 and a valve 37. After recovering $H_2O$ for a predetermined period of time, the valves 25a and 26a at the inlet and outlet ports are closed, the trapped water in the $H_2O$ recovery trap 23a is melted with a heater 40a, and the melted water is stored in an $H_2O$ recovery tank 43 through a pipe 41 and a valve 42. While the valves 25a and 26a are closed to heat the $H_2O$ recovery trap 23a with the heater 40a, valves 25b and 26b are opened to operate the cooler 30b to thereby recover $H_2O$ by the other $H_2O$ recovery trap 23b. In this manner, by switching the coolers 30a and 30b, the cooling coils 35a and 36b, the heaters 40a and 40b, and the respective valves, the pair of $H_2O$ recovery sections alternately performs the $H_2O$ cooling and solidifying step and the $H_2O$ melting step, so that water may be continuously recovered in the $H_2O$ recovery tank. The concentration of $^3H$ in the recovered $H_2O$ is measured with a liquid scintillation counter.

Figure 4:
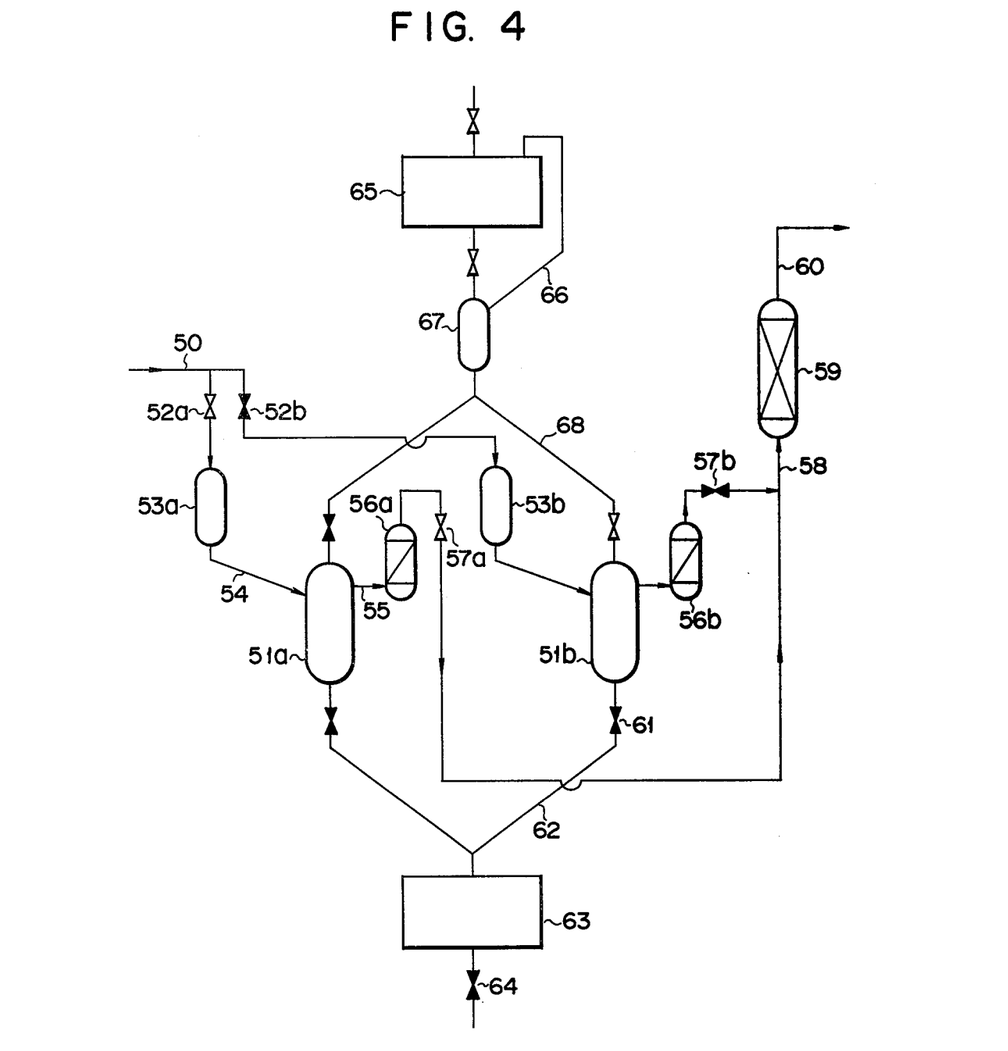
FIG. 4 is a system diagram showing an embodiment of the $CO_2$ recovery section.

An embodiment of the parallel-arranged $CO_2$ recovery sections is shown in FIG. 4. Gas passed through a gas guide line 50 is fed to one $CO_2$ recovery trap 51a of a pair of $CO_2$ recovery traps through a valve 52a, a backstopper tank 53a, and a line 54. $CO_2$ in the gas is absorbed by the monoethanolamine in the $CO_2$ recovery trap 51a. The gas eliminated of $CO_2$ is guided to a mist trap 56a through a line 55 to be deprived of mist, and then passed through a valve 57 and a line 58 to be guided to a vapor trap 59 where the monoethanolamine vapor is removed with a synthetic zeolite or the like. The gas then flows to an outlet port or a stack through a line 60. Meanwhile, valves 52b and 57b associated with the other $CO_2$ recovery trap 51b are closed, and the monoethanolamine solution containing absorbed $CO_2$ is drained to a monoethanolamine solution recovery tank 63 through a line 62. Thereafter, the valve 61 is closed, and fresh monoethanolamine is measured by a measuring tank 67 with a breather 66 and is then fed to the $CO_2$ recovery trap 51b through a line 68. Next, the $CO_2$ recovery trap 51b traps $CO_2$ while the monoethanolamine solution containing $CO_2$ within the $CO_2$ recovery trap 51a is passed to the recovery tank 63. The solution passed to the monoethanolamine recovery tank 63 from the two $CO_2$ recovery tanks 51a and 51b is recovered through a valve 64 at predetermined intervals, and the concentration of $^{14}C$ in the solution is measured with a liquid scintillation counter. In the $CO_2$ recovery sections described above, the valves are switched to alternately perform the $CO_2$ recovery step and the drain and feed step of the monoethanolamine, so as to continuously recover $CO_2$ and store the monoethanolamine solution containing $CO_2$ in the monoethanolamine recovery tank.

Figure 5:
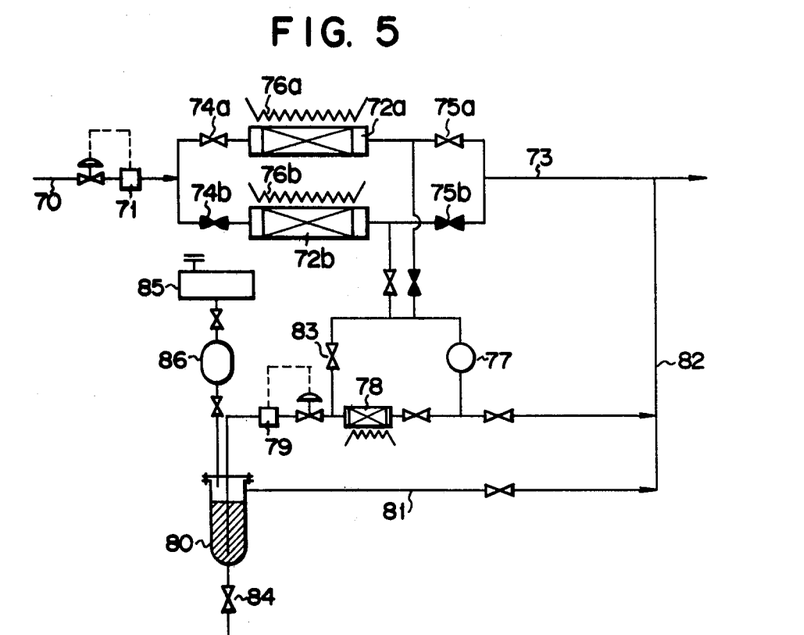
FIG. 5 is a system diagram showing another embodiment of the $CO_2$ recovery section.

Another embodiment of the $CO_2$ recovery sections will now be described with reference to FIG. 5. In this embodiment, $H_2O$ in the effluent gas is removed by a pretreatment section and $CO_2$ is recovered by the absorption method. The effluent gas is guided from a line 70 through a flowmeter 71 to one of two adsorbing columns, for example, 72a, where $CO_2$ and $H_2O$ contained in the gas are adsorbed by an adsorbent such as a synthetic zeolite. The gas is then passed to an outlet port through a line 73. At an appropriate time before the adsorption capacity of the adsorbing column 72a reaches saturation, valves 74a and 75a are closed and valves 74b and 75b are opened to operate the other adsorbing column 72b. The temperature of the adsorbing column 72a is elevated by a heater 76a for desorption of $CO_2$ and $H_2O$. The desorption gas is flowed by a pump 77 so that all or part of it is guided to an $H_2O$ adsorbing column 78. The gas is deprived of $H_2O$ by silica gel placed in the $H_2O$ adsorbing column 78 and is then guided to a $CO_2$ recovery section 80 through a flowmeter 79. $CO_2$ is then removed by absorption in the monoethanolamine, and the remaining gas flows to an outlet port through lines 81 and 82. After completion of adsorption of $CO_2$ for a predetermined period of time, $H_2O$ adsorbed at the $H_2O$ adsorbing column 78 is desorbed by heating with a heater. The gas is then evacuated by the pump 77 through a valve 83 and a line 82, and the monoethanolamine solution which had adsorbed the $CO_2$ is recovered through a valve 84. Fresh monoethanolamine, the amount of which is first measured by a measuring tank 86, is fed from a feed tank 85 to the emptied $CO_2$ recovery section 80. In this embodiment, since $CO_2$ alone in the effluent gas may be guided to the $CO_2$ recovery section, the amount of the monoethanolamine to be used may be reduced to the minimum. The operating conditions for recovering $CO_2$ when effluent gas containing $CO_2$ and $H_2O$ is supplied to an apparatus of this embodiment are shown in Table 2 below. The distribution rate in the table indicates the value of the total amount of feed gas (l) to the $CO_2$ recovery section divided by the total amount of the adsorbed gas (l) desorbed from the synthetic zeolite in the adsorbing column.

TABLE 2

| | |
|---|---|
| Flow rate of feed gas [Nl/min] | 1.0 |
| Composition of feed gas  $H_2O$ | 10,720 ppm |
| $CO_2$ | 300 ppm |
| Air | Balance |
| Recovery time [days] | 28 |
| Amount of synthetic zeolite adsorbent [gr] | 350 × 2 columns |
| Adsorbing temperature of synthetic zeolite [°C.] | 20 |
| Desorbing temperature of synthetic zeolite [°C.] | 300 |
| Switching frequency | Once/day |
| Amount of silica gel [gr] | 150 |
| Adsorbing temperature of silica gel [°C.] | 20 |
| Desorbing temperature of silica gel [°C.] | 300 |
| Amount of monoethanolamine [cc] | 105 |
| Distribution rate of desorbed gas introduced monoethanolamine in $CO_2$ recovery section | 0.25 |

As may be seen from Table 2, the amount of monoethanolamine may be reduced to about ¼ that required for the case when $CO_2$ in the effluent gas is directly absorbed without removing $H_2O$ in the pretreating section.

Figure 6:
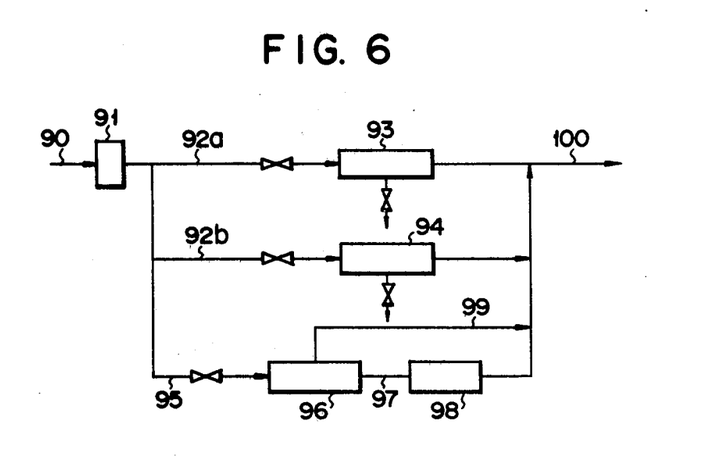
FIG. 6 is a system diagram showing another embodiment of the monitoring apparatus wherein the $H_2O$ recovery section, the $CO_2$ recovery section, and a rare gas concentrating section are arranged parallel to each other.

FIG. 6 shows the third embodiment of the present invention and shows a monitoring apparatus wherein the $H_2O$ recovery section, the $CO_2$ recovery section, and the rare gas concentrating section are arranged parallel to each other. The effluent gas from a nuclear reactor is divided in three lines from a line 90 through an oxidizer 91. One part is introduced to an H₂O recovery section 93 through a branch line 92a, and another part is introduced to a CO₂ recovery section 94 through another branch line 92b where both parts of the gas are treated as has been described with reference to FIGS. 1 to 5. The remaining part of the gas is fed to a rare gas concentrating section 96 through another branch line 95 where rare gases such as Kr and Xe are concentrated. The gas containing concentrated Kr and Xe is guided to a radiation detector 98 through a line 97 where the concentrations of radioactive $^{85}$Kr and $^{133}$Xe are measured, and these gases are passed to a line 100. On the other hand, the non-concentrated gas is returned to the line 100 through a line 99. The rare gas concentration section may adopt the membrane separation method which utilizes a gas permeable membrane which is mainly permeable to rare gases, the adsorption method according to which the rare gases are adsorbed at very low temperatures by an adsorbent such as active carbon and are thereafter desorbed, the cryogenic distillation method according to which the gas is once liquefied and the rare gases are concentrated utilizing the differences in boiling points. In the apparatus in FIG. 6, the operating conditions for the respective sections may be determined independently of each other so that optimal capacities, scales, and operating conditions may be freely selected. Furthermore, since monoethanolamine for recovering CO₂ does not enter the rare gas concentrating section, the rare gas concentrating section is not adversely affected thereby.

Figure 7:
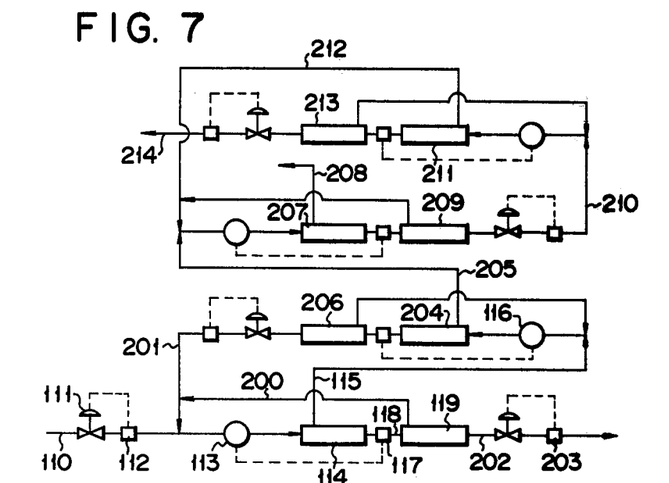
FIG. 7 is a system diagram showing an embodiment of the rare gas concentration section.

An apparatus which utilizes the membrane separation method will be shown in FIG. 7 as an example of the radioactive rare gas concentrating section shown in FIG. 6. The radioactive effluent gas flows in from a line 110, is controlled for flow rate by a valve 111 and a flowmeter 112, is compressed to a predetermined pressure by a compressor 113, and is passed to the high pressure side of a gas separating cell 114 housing a gas permeable membrane. Part of the introduced gas permeates the membrane whereby the radioactive gas is concentrated to flow out of the gas separating cell 114. The gas is then introduced to a compressor 116 of a second stage through a line 115. The non-permeated gas flows to the high pressure side of second gas separating cell 119. Part of the introduced gas permeates the membrane whereby the radioactive gas is concentrated to flow into a return line 201 from the second stage through a line 200. The gas then joins with the gas from the line 110 and enters the compressor 113 again. The non-permeated gas flows out from the gas separating cell 119 where the radioactive gas is depleted and is released to an outlet port through a line 202 and a flow rate controller 203. A similar operation is carried out at the gas separating cells of the second stage as well, and a concentrated gas of Kr and Xe is obtained from a line 205 as the gas which has permeated through a first gas separating cell 204. FIG. 7 shows a concentrating section of four stages cascade for detecting radioactive Kr alone. However, only two stages are required for detecting both Kr and Xe. By introducing the concentrated gas obtained from the line 205 to a radiation detector, β-rays of Kr and Xe may be detected. An embodiment for this is shown in Tables 3 and 4. The membrane used is a hollow membrane of silicone rubber.

TABLE 3

| Number of stages | | 2 |
|---|---|---|
| Feeding flow rate [Nl/min] | | 5.0 |
| Concentrated flow rate [Nl/min] | | 0.12 |
| Pressure at high pressure side [atm] | | 6.0 |
| Pressure at low pressure side [atm] | | 1.0 |
| Total membrane area [m²] | | 89 |
| Concentration in feed flow | $^{85}$Kr | $1.0 \times 10^{-10}$ |
| [μCi/cc] | $^{133}$Xe | $1.0 \times 10^{-10}$ |
| Concentration in concentrated | $^{85}$Kr | $3.4 \times 10^{-9}$ |
| flow [μCi/cc] | $^{133}$Xe | $4.0 \times 10^{-9}$ |

TABLE 4

| Stage No. | Gas separating cell | Gas flow rate [Nl/min] | | | | Membrane area [cm²] | Concentration at each section [× 10⁻¹⁰ μCi/cc] | | |
|---|---|---|---|---|---|---|---|---|---|
| | | Feed flow | Pump section | Concentrated flow | Depleted flow | | Feed flow | Concentrated flow | Depleted flow |
| 1 | Cell 114 | 5.6 | 49 | 0.73 | 4.9 | 11,000 | Kr: 1.0 | Kr: 6.9 | Kr: 0.16 |
| | Cell 119 | | | | | 810,000 | Xe: 0.89 | Xe: 6.8 | Xe: 0.0054 |
| 2 | Cell 204 | 0.73 | 6.2 | 0.12 | 0.61 | 1,500 | Kr: 6.9 | Kr: 34 | Kr: 1.4 |
| | Cell 206 | | | | | 71,000 | Xe: 6.8 | Xe: 40 | Xe: 0.015 |

When the lower limit of detection of the β-ray detector is $1 \times 10^{-9}$ μCi/cc, no detection may be made at the concentration of the feed flow. However, Kr may be concentrated to 34 times and Xe may be concentrated to 40 times the original concentrations by the two stages of concentrating steps of this apparatus, so that detection of β-rays of $^{85}$Kr and $^{133}$Xe may be facilitated.

For detecting desired components of the radioactive rare gases, for example, radioactive Kr, concentrated Kr gas is obtained by a concentrating apparatus of four stages cascade as shown in FIG. 7. In this case, the gas concentrated through the gas separating cells of the first and second stages and containing Kr and Xe passes through the line 205 and is fed to a first gas separating cell 207 of the third stage. The gas which has permeated through the first gas separating cell 207 is guided to an outlet port through a line 208, and the non-permeated gas is introduced to a second gas separating cell 209. The non-permeated gas from the second gas separating cell 209 reaches a line 210 to a first gas separating cell 211 of the fourth stage, and the gas permeated therethrough is returned to the feed line 205 to the third stage. The non-permeated gas is introduced to a second gas separating cell 213 of the fourth stage. The non-permeated gas from the second gas separating cell 213 passes through a line 214 to be fed to a radiation detector. In the third and fourth stages, the operation of separating Kr from the gas which been concentrated by the operation up to the second stage and which contains both Kr and Xe is achieved by mainly depleting Xe by controlling the membrane areas and the flow rates corresponding to the respective gas separating cells. An embodiment for achieving this operation is shown in Tables 5 and 6.

TABLE 5

| | | |
|---|---|---|
| Number of stages | | 4 |
| Feeding flow rate [Nl/min] | | 16 |
| Concentrated flow rate [Nl/min] | | 0.20 |
| Pressure at high pressure side [atm] | | 6.0 |
| Pressure at low pressure side [atm] | | 1.0 |
| Total membrane area [m$^2$] | | 50 |
| Concentration in feed flow [μCi/cc] | $^{85}$Kr | $1 \times 10^{-10}$ |
| | $^{133}$Xe | $1 \times 10^{-9}$ |
| Concentration in concentrated flow [μCi/cc] | $^{85}$Kr | $2 \times 10^{-9}$ |
| | $^{133}$Xe | $1 \times 10^{-10}$ |

TABLE 6

| Stage No. | Gas separating cell | Gas flow rate [Nl/min] | | | | Membrane area [cm$^2$] | Concentration at each section [$\times 10^{-10}$ μCi/cc] | | |
|---|---|---|---|---|---|---|---|---|---|
| | | Feed flow | Pump section | Concentrated flow | Depleted flow | | Feed flow | Concentrated flow | Depleted flow |
| 1 | Cell 114 | 9.0 | 79 | 1.2 | 7.8 | 18,000 | Kr: 1.0 | Kr: 6.9 | Kr: 0.16 |
| | Cell 119 | | | | | 1,300,000 | Xe: 0.89 | Xe: 6.8 | Xe: 0.0054 |
| 2 | Cell 204 | 1.2 | 10 | 0.20 | 0.98 | 2,500 | Kr: 6.9 | Kr: 34 | Kr: 1.4 |
| | Cell 206 | | | | | 110,000 | Xe: 6.8 | Xe: 40 | Xe: 0.015 |
| 3 | Cell 207 | 0.20 | 2.0 | 0.0056 | 0.20 | 65 | Kr: 42 | Kr: 440 | Kr: 31 |
| | Cell 209 | | | | | 21,000 | Xe: 40 | Xe: 1400 | Xe: 1.1 |
| 4 | Cell 211 | 0.20 | 1.9 | 0.0054 | 0.19 | 63 | Kr: 31 | Kr: 330 | Kr: 22 |
| | Cell 213 | | | | | 20,000 | Xe: 1.1 | Xe: 40 | Xe: 0.07 |

The content of Xe in the gas from the line 214 is $7 \times 10^{-12}$ μCi/cc; since this is below the lower limit for detection by the radiation detector, Kr of $2.2 \times 10^{-9}$ μCi/cc alone may be detected.

Figure 8:
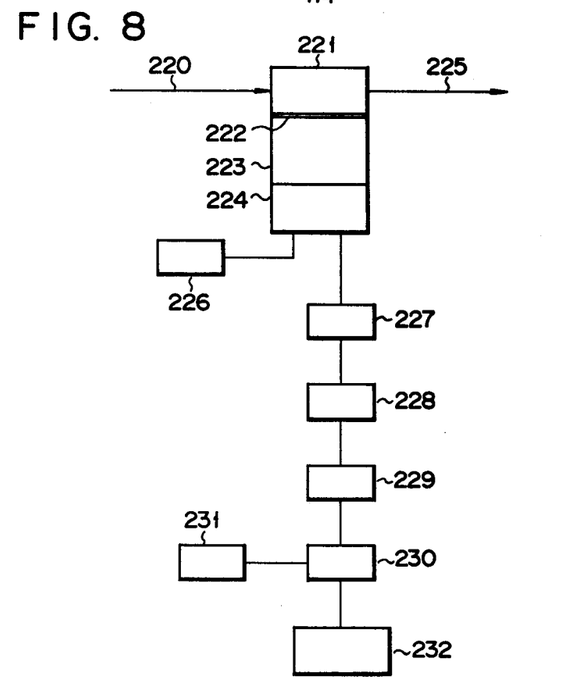
FIG. 8 is a system diagram showing a radiation detection instrument.

An embodiment of the radiation detector will be described with reference to FIG. 8. The gas which has been introduced through a line 220 is fed to a gas chamber 221 inside a detector main body comprising the gas chamber 221, a plastic scintillator plate 222, a photomultiplier 223, and a divider network 224. The radioactivity of the gas is detected there, and the gas is passed out from a line 225. The radiation from the gas introduced inside the gas chamber 221 emits light by the plastic scintillator plate 222. The light emitted in this manner is received by the photomultiplier 223, and is obtained as electric signals from the divider network 224 at which a high voltage is applied from a power source 226. These signals are amplified by a preamplifier 227 and a linear amplifier 228, and signals of energy exceeding a lower limit set by an amplitude discriminator 229 are selected. The selected signals corresponding to Kr alone are measured by a counter 230, and are output from a printer 232 at a frequency which is predetermined by a timer 231.

Figure 9:
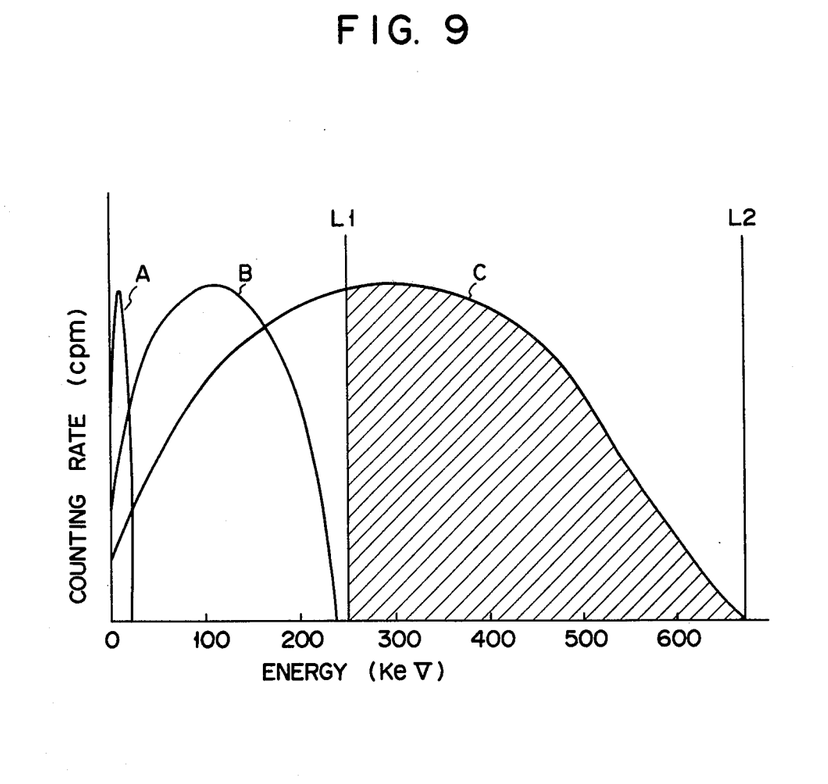
FIG. 9 is a graph showing the energy distribution of the radioactive nuclides to be detected.

Using such a radiation detector, 10 sheets of plastic scintillator plates (manufactured by Nuclear Enterprise Co. Ltd., U.K.) of 100 mm diameter were housed within a gas chamber of 991 cc capacity and enclosed by iron material of 14 mm thickness. To the photomultiplier (RCA 8575 manufactured by RCA Co. Ltd., U.S.A.) was applied $-2,000$ V. The gas containing $^{85}$Kr of $1.2 \times 10^{-5}$ μCi/cc was fed at a flow rate of 100 cc/min, and the amplitude discriminator was set with a lower limit L1 of 0.2 V and an upper limit L2 of 5.5 V. A measurement of 47,000 cpm was then obtained. With this detector, even when isotopes of $^3$H and $^{14}$C are mixed in, signals C corresponding to $^{85}$Kr may be measured to distinguish from signals A corresponding to $^3$H and signals B corresponding to $^{14}$C, by appropriately selecting the lower limit L1 and the upper limit L2 as shown in FIG. 9.

Figure 10:
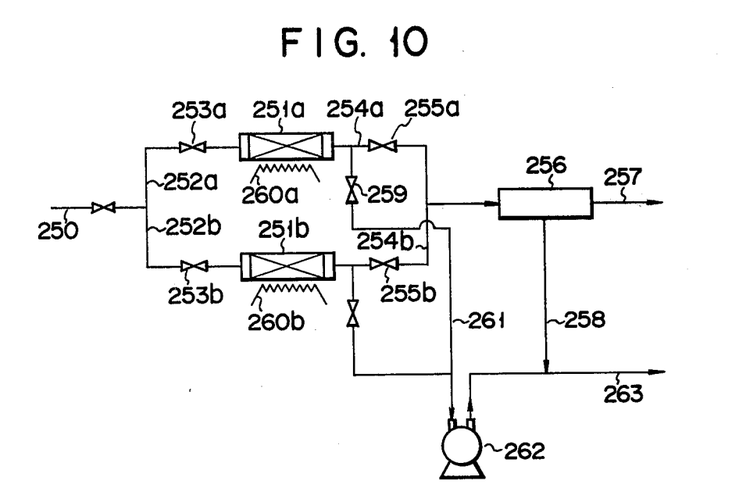
FIGS. 10 and 11 are system diagrams showing other embodiments of the rare gas concentrating section, respectively.

Another embodiment of the rare gas concentrating apparatus will be described with reference to FIG. 10. With this apparatus, $CO_2$ and $H_2O$ are eliminated by a pretreatment and rare gas concentration is performed thereafter. Radioactive effluent gas treated by an oxidizer (not shown) is fed from a line 250 and is introduced to one adsorbing column 251a of a pair of parallel-arranged adsorbing columns 251a and 251b where $CO_2$ and $H_2O$ in the gas are adsorbed and thus eliminated by an adsorbent such as a synthetic zeolite placed in the adsorbing column 251a. The gas deprived of $CO_2$ and $H_2O$ is fed to a rare gas concentrating section 256 through a line 254a and a valve 255a, and the concentrated rare gas is discharged from a line 257 and the depleted gas is discharged from a line 258. At an appropriate time before the adsorption capacity of the adsorbing column 251a reaches saturation, valves 253a and 255a are closed and a valve 259 is opened. The adsorbing column 251a is heated by a heater 260a to desorb $CO_2$ and $H_2O$. The column 251a is evacuated by an evacuation pump 262 through the valve 259 and a line 261 so as to discharge the gas containing $CO_2$ and $H_2O$ from a line 263. Meanwhile, the gas deprived of $CO_2$ and $H_2O$ is fed to the rare gas concentrating section 256 through a system of line 252b, valve 253b, adsorbing column 251b, valve 255b, and line 254b. As has been described, in this embodiment, the system of the adsorbing column 251a and the system of the adsorbing column 251b are alternately switched to perform adsorption and desorption of $H_2O$ and $CO_2$. Simultaneously, the effluent gas deprived of $H_2O$ and $CO_2$ is continuously concentrated by the rare gas concentrating section for feeding it to the radiation detector through the line 257. With such an apparatus, since the concentrated rare gases do not contain $H_2O$ or $CO_2$, the electrical operation for preventing the adverse effects of $^3$H and $^{14}$C during radiation measurement as shown in FIG. 9 becomes unnecessary, thus advantageously improving the detection sensitivity.

Figure 11:
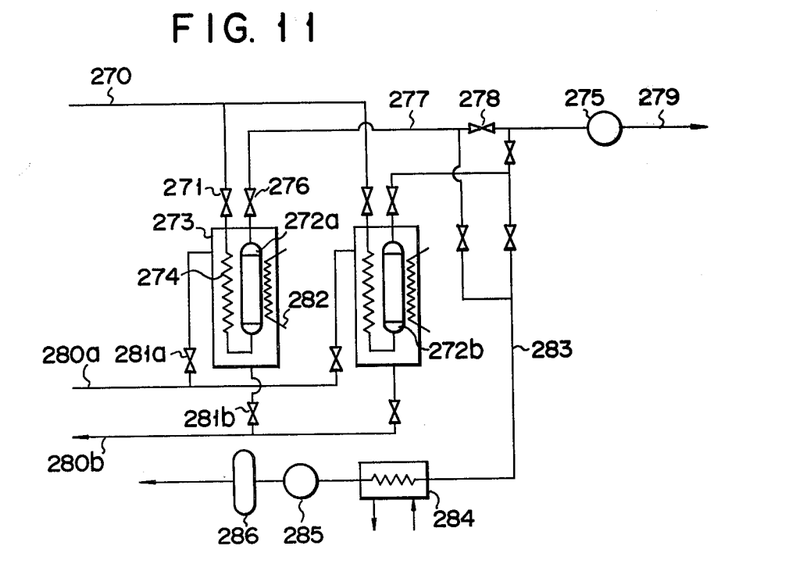

An embodiment of the rare gas concentrating section adopting the adsorption method will be described with reference to FIG. 11. Radioactive effluent gas fed from a line 270 is passed through a valve 271, a pre-cooling pipe 274 and an adsorbing column 272a inside a heat insulator 273. The gas cooled at the pre-cooling pipe 274 is brought into contact with active carbon inside the adsorbing column 272a. There, mainly rare gases Kr and Xe are adsorbed, and the remaining gas is discharged by a pump 275 though a valve 276, a line 277, a valve 278, and a line 279. At an appropriate time before the adsorption capacity of the adsorbing column 272a reaches saturation, valves 281a and 281b are closed, and the flow of a coolant from a line 280a through the heat insulator 273 to a line 280b is interrupted. The valve 271 is closed, and the adsorbing column 272a is heated to a predetermined temperature by a heater 282. Most of the air is desorbed and discharged by the pump 275 through the valve 276 and the line 279. Thereafter, the valve 278 is closed and the adsorbing column 272a is further heated by a heater 282 to a higher temperature to desorb the rare gases such as Kr and Xe. The gases are then returned to room temperature by a heat exchanger 284 through a line 283. The gases are then guided to the radiation detector through a pump 285 and a reservoir tank 286. The radioactive effluent gas fed from the line 270 during the desorbing operation of the adsorbing column 272a is similarly desorbed at a second adsorbing column 272b. By thus switching the two adsorbing columns alternately for performing adsorption and desorption of the rare gases, the concentration and recovery of the rare gases may be performed continuously. An example will be shown in Table 7 below wherein Kr and Xe are adsorbed in active carbon for 24 hours from air containing Kr and Xe using the apparatus as described above, the air is desorbed at 0° C., and the rare gases are desorbed at 300° C. thereafter.

TABLE 7

| Flow rate of feed gas [Nl/min] | | 5.0 |
|---|---|---|
| Concentration in feed gas | Kr | $1 \times 10^{-10}$ |
| [$\mu$Ci/cc] | Xe | $1 \times 10^{-11}$ |
| | Air | Balance |
| Weight of active carbon adsorbent [gr] | | 100 |
| Switching time [hr] | | 24 |
| Adsorbing temperature [°C.] | | $-50$ |
| Desorbing temperature (1) [°C.] | | 0 |
| Desorbing temperature (2) [°C.] | | 300 |
| Concentration in | Kr | $2 \times 10^{-9}$ |
| concentrated gas | Xe | $2 \times 10^{-9}$ |
| [$\mu$Ci/cc] | Air | Balance |

When the lower limit of detection of the $\beta$-ray detector is $1 \times 10^{-9}$ $\mu$Ci/cc in this example, the $\beta$-rays may not be detected at this rare gas concentration in the feed gas. However, since this apparatus is capable of enriching the concentration of Kr 20 times and that of Xe 200 times, $^{85}$Kr and $^{133}$Xe may be detected by the $\beta$-ray detector. When the rare gas concentrations in the feed gas are still lower, the desired concentration degree may be obtained by performing the adsorption at lower temperatures.

In summary, in accordance with the present invention, since the H$_2$O recovery sections for recovering $^3$H, the CO$_2$ recovery sections for recovering $^{14}$C, and the rare gas concentrating sections for concentrating the radioactive rare gases are arranged parallel to each other, the gas flow rates, capacities and scales of the respective parts may be arbitrarily selected independently of each other, and the respective sections may be operated independently of each other. Therefore, as compared with a conventional apparatus wherein the respective sections are arranged serially, the apparatus of the invention may be made compact in size and simplified, making the maintenance and control easier. Furthermore, since the monoethanolamine for recovering CO$_2$ does not enter the rare gas concentrating section, the adverse effects which may otherwise be caused may be eliminated.

What is claimed is:

1. A radioactive effluent gas monitoring apparatus for deteting radioactive nuclides contained in radioactive effluent gas from a nuclear facility, comprising:
   a guide line for discharging effluent gas from the nuclear facility;
   a water recovery section for recovering $^3$H in the effluent gas in the form of H$_2$O;
   carbon dioxide recovery section connected parallel to said water recovery section and recovering $^{14}$C in the effluent gas in the form of CO$_2$;
   branch lines for separately feeding the effluent gas from said guide line to said water recovery section and said carbon dioxide recovery section;
   a line for joining output gases from said water recovery section and said carbon dioxide recovery section to return the joined gas to the nuclear facility; and
   detecting means for detecting radioactivities in the recovered H$_2$O and CO$_2$.

2. An apparatus according to claim 1, wherein two each of said H$_2$O recovery sections and said CO$_2$ recovery sections are arranged parallel to each other.

3. An apparatus according to claim 1 or 2, wherein said CO$_2$ recovery section has a pretreatment section for adsorbing and eliminating H$_2$O in the effluent gas, said CO$_2$ recovery section recovering CO$_2$ through absorption by monoethanolamine.

4. An apparatus according to claim 3, wherein said pretreatment section further includes an adsorbing column capable of adsorbing CO$_2$ and H$_2$O by adsorbent and desorbing, the desorbed gas from the desorbing column being introduced to said pretreatment section to eliminate H$_2$O.

5. An apparatus according to claim 1 or 2, wherein said guide line has an oxidizing section for converting carbon monoxide, hydrogen, and hydrogen carbide in the effluent gas to water and carbon dioxide.

6. An apparatus according to claim 1, wherein a rare gas concentration section for recovering and concentrating rare gases in the effluent gas is further arranged parallel to said water recovery section and said carbon dioxide recovery section, respectively, and a radiation detector for detecting radioactivity in the concentrated rare gases is further incorporated.

7. An apparatus according to claim 6, wherein said rare gas concentration section has a pretreatment section for eliminating CO$_2$ and H$_2$O in the effluent gas.

8. An apparatus according to claim 1, wherein said H$_2$O recovery section includes a device which cools the effluent gas to condense or solidify water and thereby separate it, and which elevates the temperature thereafter to liquefy the separated water; or a device which adsorbs water with an adsorbent and which elevates the temperature thereafter to desorb the water.

9. An apparatus according to claim 1, wherein said CO$_2$ recovery section includes a device which absorbs CO$_2$ with a CO$_2$ absorbing solvent, or a device which adsorbs CO$_2$ with an adsorbent and which elevates the temperature thereafter to desorb the CO$_2$.

10. An apparatus according to claim 6, wherein said rare gas concentration section includes a gas separating cell having a gas permeable membrane, or a device which adsorbs rare gases with an adsorbent and which elevates the temperature thereafter to desorb the rare gases.

11. An apparatus according to claim 6 or 10, wherein the rare gas concentration section includes gas separating cells having gas permeable membranes and capable of condensing krypton alone.

* * * * *

UNITED STATES PATENT AND TRADEMARK OFFICE
CERTIFICATE OF CORRECTION

PATENT NO. : 4,435,644
DATED : March 6, 1984
INVENTOR(S) : Hideaki Heki

It is certified that error appears in the above-identified patent and that said Letters Patent is hereby corrected as shown below:

On the title page add: --[30] Foreign Application Priority Data

[30] Jul. 15, 1980 [JP] Japan .............. 55/95673--

Signed and Sealed this

Twenty-fourth Day of July 1984

[SEAL]

Attest:

GERALD J. MOSSINGHOFF

Attesting Officer    Commissioner of Patents and Trademarks